United States Patent [19]
Storz

[11] Patent Number: 5,439,461
[45] Date of Patent: Aug. 8, 1995

[54] GRIP FOR A SURGICAL INSTRUMENT

[76] Inventor: Martin Storz, Schauinslandstrasse 1, D-78532 Tutlingen, Germany

[21] Appl. No.: 217,452

[22] Filed: Mar. 24, 1994

[30] Foreign Application Priority Data

Mar. 24, 1993 [DE] Germany .................. 43 09 569.0

[51] Int. Cl.⁶ .............................................. A61B 17/32
[52] U.S. Cl. ........................................ 606/1; 606/205; 606/171; 606/174
[58] Field of Search ................. 606/1, 171, 174, 205, 606/206, 207; 128/751, 754

[56] References Cited

U.S. PATENT DOCUMENTS

| | | | |
|---|---|---|---|
| 4,644,651 | 2/1984 | Jocobsen | 606/174 X |
| 5,160,343 | 11/1992 | Brancel et al. | 606/205 |
| 5,174,300 | 12/1992 | Bales et al. | 606/205 X |
| 5,184,625 | 2/1993 | Cottone, Jr. et al. | 606/206 X |
| 5,211,655 | 5/1993 | Hasson | 606/205 |
| 5,312,433 | 5/1994 | Boebel | 606/205 |
| 5,330,496 | 7/1994 | Alferness | 606/171 |

Primary Examiner—Peter A. Aschenbrenner
Attorney, Agent, or Firm—Dominik & Stein

[57] ABSTRACT

The invention concerns a grip for a tubular shafted surgical instrument having two grip parts. The grip parts have grip contact surfaces which run generally parallel to each other and to the shaft tube. The first grip part is securely attached to the shaft tube, while the second grip part is pivotable as a rocker and engages the operational element of the tubular shaft instrument.

17 Claims, 2 Drawing Sheets

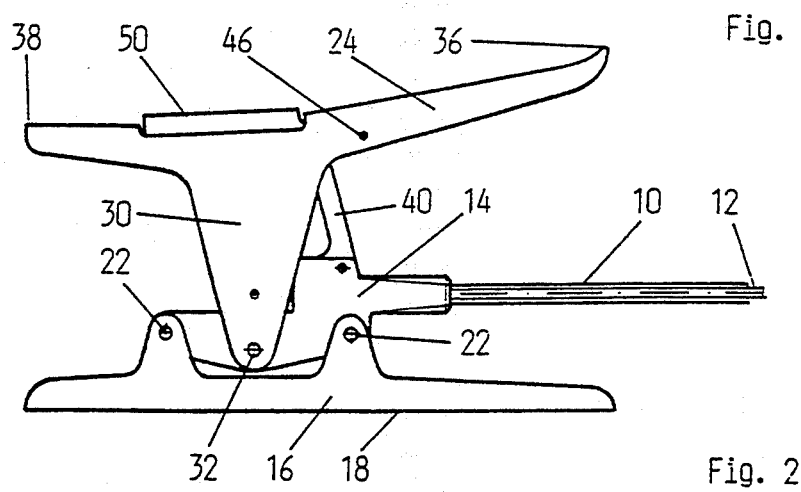
Fig. 1
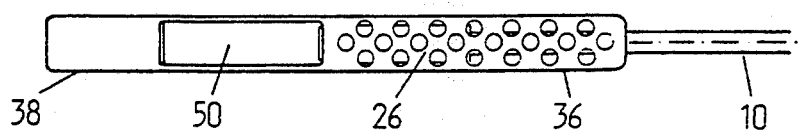
Fig. 2
Fig. 4
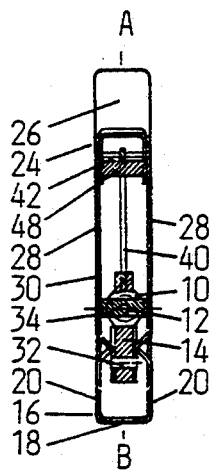
Fig. 3
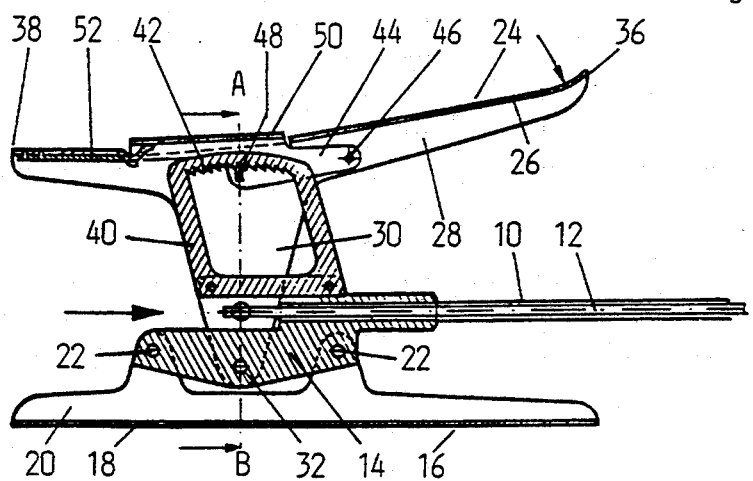
Fig. 5
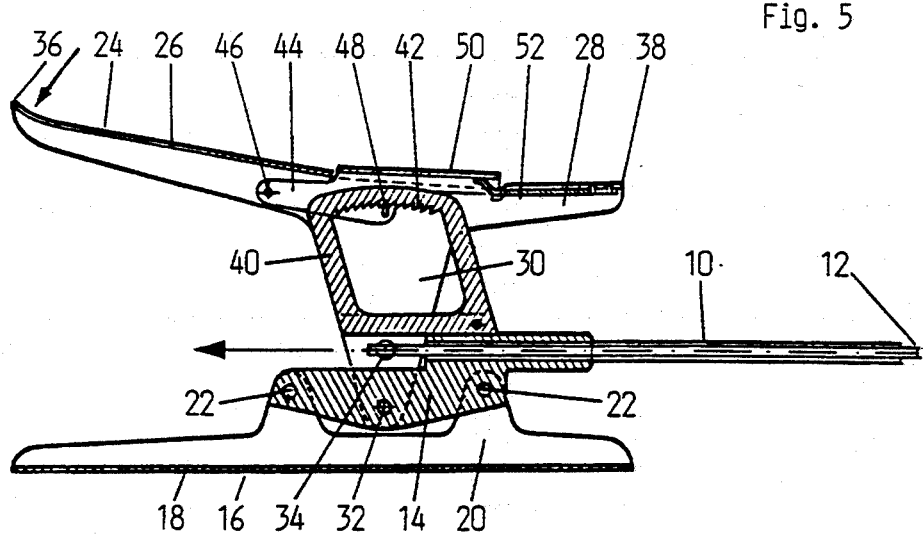

GRIP FOR A SURGICAL INSTRUMENT

BACKGROUND OF THE INVENTION

1. Field of the Invention

The invention concerns a grip for a tubular shafted surgical instrument having two grip parts. The grip parts have grip contact surfaces which run generally parallel to each other and to the shaft tube. The first grip part is securely attached to the shaft tube, while the second grip part is pivotable as a rocker and engages the operational element of the tubular shaft instrument.

2. Description of the Related Art

Tubular shaft instruments of many types are used in arthroscopic and in minimally invasive surgery. The tubular shafted instruments are comprised of a tubular shaft in which an operative element is axially slidably mounted. The axial sliding of the operative element with respect to the tubular shaft results in operation of the jaws which are provided on the distal end of the tubular shafted instrument, that is, in general operating brings about a closing of the jaws. The operation of the jaws can be accomplished by a pushing of the operational element within the tubular shaft, for which the operational element must have sufficient stiffness, for example, as a rod or internal tube. If the operation of the jaws is accomplished by an axial pulling of the operational element, then such a stiffness of the operational element is not required, and the construction of the operational element is not limited to a rod or internal tube, but can be constructed of a flexible draw cable.

The known tubular shafted instruments are comprised, in most cases, of a scissor grip with two ring-grip parts which are pivotally mounted with respect to each other. The first grip part is fixedly connected to the tubular shaft, while the second grip part is connected to the operational element. The two grip parts are offset at an angle of up to 90° relative to the axis of the tubular shaft, and lie in the plane of operational movement of the jaws of the tubular shaft instrument. Should it be necessary during operation to change the operational plane of the jaws, for example the plane of the cutting or gripping action of the jaws, then the operator must correspondingly twist the hand which is manipulating the controls. This can lead to an ergonomicaly uncomfortable hand position, which in particular in lengthy operations can lead to significant fatigue. For operating the jaws of the tubular shaft instrument the grips are moved towards each other under pressure. For the opening of the jaws the rings, in which the fingers of the operator are inserted, are forced apart. In the course of such an opening movement it is very difficult to stably manipulate the tubular shaft instrument and particularly the jaws.

There are also known scissor grips with ringless grip parts, in which the grip parts are pressed towards each other for the operation of the jaws, and in which for the opening movement they are spread apart by means of a spring mechanism. When using such an instrument it is necessary to almost completely relax the grip in order to permit the jaws to open, so that the controlling of the instrument is even more difficult.

SUMMARY OF THE INVENTION

The present invention is concerned with the task of providing a grip for a surgical instrument, with which the closing as well as the opening movement of the jaws is possible under stable control of the hand of the operator.

This task is inventively accomplished by means of a grip for a surgical instrument, the surgical instrument comprising a tubular shaft having a proximal end and a distal end, at least one articulated jaw mounted on the distal end of the tubular shaft, a first grip part which is fixedly connected to the proximal end of the tubular shaft, a second grip part mounted pivotally about a pivot axis which pivot axis is perpendicular to the shaft tube, and an elongated operational element slidably disposed in the tubular shaft for conveying operational forces from the second grip part to at least one of the jaws, wherein the first grip part and the second grip part respectively exhibit grip contact surfaces which are spaced apart from each other and describe an angle of less than 30°, and wherein the second grip part is constructed as a rocker with an actuation arm and a return arm and is pivotable about the pivot axis and is connected with the operational element in such a manner that upon pressure to the actuating arm or to the return arm the elongated operational element is axially displaced in the tubular shaft in an operational direction or a return direction, respectively.

Preferred embodiments of the invention are set forth below and claimed in the dependent claims.

In accordance with the invention the tubular shaft instrument exhibits two grip surfaces which are positioned essentially parallel to each other. The first grip part is fixedly connected with the tubular shaft, while the second grip part is provided as a rocker. When using the tubular shaft instrument the operator grasps the grip is such a manner that his hand encompasses both grips. The closing of the jaws is accomplished by application of pressure by the hand upon one of the arms if the second grip piece, the grip piece being constructed as rocker, and the opening of the jaws is accomplished by pressing upon the other arm of this second grip piece, namely the return arm. In the closing operation as well as in the opening-returning operation there is present the pressure contact between the hand and the two grip parts. There thus results in the closing as well as in the opening operation a stable control of the grip and thereby of the jaws of the tubular shaft instrument.

In the case that the two grip parts are provided essentially parallel to the axis of the tubular shaft instrument, then it becomes possible to operate Over a relatively wide range of angles of the pivot plane relative to the hand by swiveling the position of the second grip part. The operator can thus rotate the grip over a wide range of angles in his hand, in order to rotate the operating plane of the jaws of the tubular shaft instrument in the field of operation, without having to change the position of his hand.

Since the grip surfaces of the hand are provided essentially parallel to each other, that is, encompass an angle of less than 30°, the grip lies comfortably in the hand and the pivoting of the second grip part for closing as well as for opening of the jaws is actuated essentially by closing pressure of the hand. This manipulation is ergonomically becoming and can be carried out without fatigue even over lengthy operations. In order that the operational movement, which in practice as a rule is the closing of the jaws, can be carried out with delicate feel as well as with great force when necessary, it is preferred that the second grip part be constructed asymmetrically and, for urging of the operating element in the operating direction, exhibits a longer actuation arm for urging against the first grip part. The return movement of the operating element, which as a rule brings about an opening of the jaws, is accomplished by pressure upon the return arm which is shorter than the opposing actuation arm. The return movement can also be assisted by means of a return spring. For many applications it would be of advantage to provide the grip with a ratchet, which fixes the position of the grip parts and thereby the position of the jaws in the respective operating positions. For this a detente latch is preferably provided on the second grip part, which is urged by means of a spring into a fixed locking ratchet. A convenient release of the detente can thereby be made possible, in that a latch disengagement key is provided integrally in the grip surface of the second grip part. It is preferred that the detente release is integrated in the grip surface in the realm of the return arm of the second grip part, so that a depressing of detente release can be accomplished at the same time as a returning actuation of the return arm. In a further embodiment the release of the detente can be accomplished by the depression of the entire second grip part.

A particularly preferred embodiment with regard to ease of construction and production technology results when the tubular shaft is seated in a block-shaped receptacle and the two grip parts are respectively constructed as fitting shanks. The ratchet can then be provided on this receptacle or the shank of the first grip part, whereby the detente latch can be disposed between the shanks of the second grip part and be enclosed thereby. The entire locking mechanism is provided thusly within the confines of contour of the grip, where it does not come into contact with the hand of the operator and does not interfere with the manipulation of the grip. The locking mechanism can not cause any injury to the hand or the glove of the operator and can not get snagged on clothing, towels, suture material, etc.

BRIEF DESCRIPTION OF THE DRAWING

In the following the invention will be further illustrated by means of illustrative embodiments as shown in the figures. There can be seen:

FIG. 1 a side view of a grip for a tubular shafted instrument in a first embodiment, FIG. 2 a top view of the grip of FIG. 1, FIG. 3 an axial lengthwise section of the grip of FIG. 1, FIG. 4 a section along the line A–B in FIG. 3, FIG. 5 a section as in FIG. 3 of a second embodiment of the grip, FIG. 6 a section as in FIG. 3 showing a third embodiment of the grip, FIG. 7 a section as in FIG. 3 showing a fourth embodiment of the grip, FIG. 8 a section along the line A–B in FIG. 7, and FIG. 9 a section as in FIG. 3 showing a fifth embodiment of the grip.

DETAILED DESCRIPTION OF THE INVENTION

Figure 6:
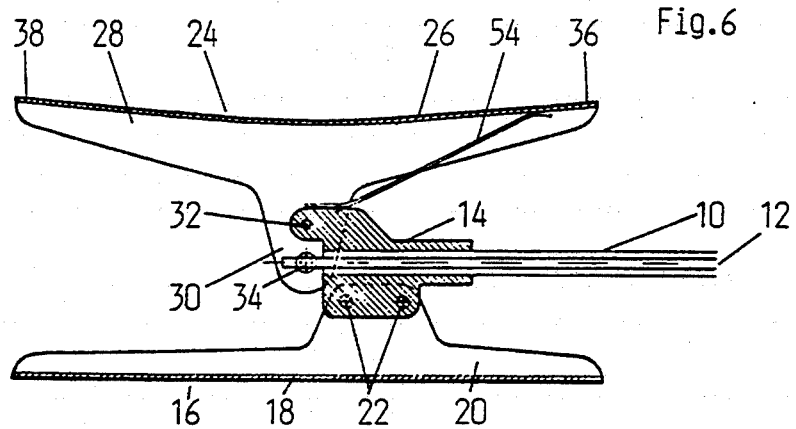

In the first embodiment as shown in FIGS. 1–4 the tubular shaft instrument comprises an outer shaft tube 10, in which an operational element 12 in the form of a rod is axially slidably provided. On the not-shown distal end of the tubular shafted instrument there are provided jaws of the type which are of themselves known in the art, which by means of the respective in-and-outward sliding of the operating element 12 relative to the shaft tube 10 are operated. The proximal end of the shaft tube 10 is set into a receiving part 14, which is constructed of a milled or stamped metal part or a cast part in the form of a flat block provided with a receptacle borehole. The operating element 12 is directed out of the rear out of the proximal end of the shaft tube 10 and out of the receiving part 14.

The first grip part 16 is rigidly connected with the receiving part 14. The first grip part 16 shows a grip surface 18, which is in the form of an elongated right-angled strip, which runs parallel to the axis of the shaft tube 10. On both sides of the grip surface 18 there are shanks 20 bent at right angles to the grip surface 18, so that the grip part 16 exhibits a "U" shape as can be seen in cross-section FIG. 4. The shanks 20 are respectively attached at two points 22 on the two flat sides of the receptacle part 14, for example, by means of rivets or spot welds.

A second grip part 24 is correspondingly provided with an elongated small right-angled grip surface 26, from which two shanks 28 are bent at right angles to form a "U" shaped cross section. The grip surface 26 of the second grip part 24 is likewise oriented essentially parallel to the axis of the shaft tube 10. The grip surfaces 18 or 26 of the grip part 16 or 24 run parallel to each other and are spaced apart from each other. In the central region of the stretched out part of the second grip part 24 the two shanks 28 are mounted on an attachment protrusion 30 which projects perpendicularly from the grip surface 26. The free ends of the protrusions 30 of the shanks 28 contact on the two flat sides of the receiving piece 14 and are mounted pivotally with respect to the receiving part by means of a mounting pin 32 inserted in the receiving part 14. Thereby the second grip part 24 is pivotable as a rocker about the mounting pin as pivot axis.

Between the mounting pin 32 and the grip surface 26 there is a bridge piece 34 disposed diagonally between the shanks 28, on which the proximal end of the operating element 12 is articulated. The rocking type pivot movement of the second grip part 24 brings about thereby an axial displacement of the operational element 12 in the shaft tube 10.

In the working example of FIGS. 1–4 the second grip part 24 is constructed asymmetrically with respect to the pivot axis defined by lodging pin 32, in the axis of the shaft tube 10 vertical plane, such that there is formed a grip surface 26 of a longer distal oriented actuating arm 36 and a shorter proximal oriented return arm 38. In the operation of the tubular shafted instrument the operator encloses with his hand the grip parts 16 and 24. If he presses thereby the actuator arm 36 of the second grip part 24 against the first grip part 16, so will the operational element 12 in the shaft tube 10 be pushed towards the front and the jaws of the tubular shafted instrument be actuated, which in general means closed. As a result of the greater length of the actuator arm 36 a fine feel of manipulation of the jaws with great pressure is possible.

Superior of the bridge piece 34 and on the receiving part 14 a frame member 40 is provided, which is attached for example by means of spot welding in an axial slot of the receiving part 14. The frame member 40 is between the shanks 28 from inside against the grip surface 26 of the second grip part 24 oriented and has the form of a flat plate with an inner cut away. On its on the grip surface 26 bordering and thereto generally parallel running inner edge the frame member 40 displays a locking ratchet 42. A latch lever 44 is provided between the shanks 28 of the second grip part 24 and is pivotally mounted in the vicinity of the actuating arm 36 by means of an between the shank 28 inserted cross pin 46. The latch lever 44 exhibits a detente latch 48, which engages with the locking ratchet 42. Further, there is provided in the latch lever 44 a disengagement key 50, which in the essential surface formation resides in a cutout slot of the grip surface 26 in the area of the return arm 38. A latch spring 52 formed as a leaf spring is provided inside in the grip surface 26 in the area of the return arm 38, for example, by means of spot welding, and abuts with its free end from inside on the surface of the disengagement key 50. The latch spring 52 presses therewith the latch lever 44 (as shown in FIG. 3 in the primary sense) against the grip surface 26, so that the detente latch 48 engages in the locking ratchet 42 under tension of the latch spring 52 and the disengagement key 50 is provided in the grip surface 26 either snugly or slightly elevated.

When the actuation arm 36 is depressed in order to operate the jaws of the tubular shafted instrument, the detente latch 48 will ratchedly glide over the teeth of locking ratchet 42 which are inclined so as to permit this. A return tilting of the second grip part 24 and thereby an opening of the jaws against the operating direction is prevented by the detente latch 48 which is lodged in the locking ratchet 42. In the case that the jaws should be returned to the starting position, which in the general case is the open position, so the operator presses down on the disengagement key 50 against the force of the latch spring 52 and lifts thereby the detente latch 48 out of the locking ratchet 42. Upon pressing of the return arm 38 the second grip part can now (contrary to the primary operation shown in FIG. 3) be pivoted back, whereby the operational element 12 is retracted within the shaft tube 10. Since the disengagement key 50 essentially is located in the vicinity of the return arm 38, the disengagement key 50 is not operated when pressure is applied upon the actuator arm 36. The depressing of the disengagement key 50 and the pressure force upon the return arm 38 can, in comparison, be simultaneously exercised.

Since the grip surfaces 18 and 26 of the two grip parts 16 and 24 run essentially parallel to each other and to the shaft tube 10, the two grip parts 16 and 24 can be enclosed by the hand of the operator and be operated, without there being any great dependence upon the plane of operation of the grip parts 16 and 24 in the hand of the operator. The operator thus has a great freedom in the positioning of his hand relative to the operating plane of the jaws of the tubular shafted instrument.

As is readily apparent, the grip surfaces 18 and 26 need not be provided precisely parallel to each other and to the shaft tube 10. A departure is necessitated by the fact that the second grip part 24 is pivotable. In order to take advantage of the full possibilities of operation of the grip, during which the operator encompasses both grip parts 16 and 24 with his hand, it is nevertheless necessary that the grip surfaces 18 and 26 do not describe any greater angle than about 30°.

FIG. 5 shows a departure from the grip of FIGS. 1–4. Corresponding parts are indicated with the same reference numerals as previously, and reference is made to the relevant previous discussion.

The illustrative example according to FIG. 5 corresponds essentially with the illustrative example according to FIGS. 1–4 in regard to construction. The single difference resides in the fact that the longer actuation arm 36 of the second grip part 24 is directed proximally, while the shorter return arm 38 is towards the distal. By depressing of the actuating arm 36 the operational element 12 is pulled in the shaft tube 10 towards the rear, so that the jaws of the tubular sheafted instrument are manipulated by pulling of the operational element 12.

Consequently also the latch lever 44 with the disengagement key 50 and the latch spring 52 are provided in mirror image relationship to the illustrative example of FIGS. 1–4 and the teeth of locking ratchet 42 are so inclined, that the detente latch 48 which is pretensioned by means of latch spring 52 can glide over the teeth of the locking ratchet 42 when the second grip part 24 as shown in FIG. 5 is pivoted in the direction counter to the primary sense.

FIG. 6 shows a further departure of the grip. Here also corresponding parts are indicated with the same reference numerals as previously, and reference is made to the relevant previous discussion.

While in the illustrative examples of FIGS. 1–4 and in FIG. 5 the bridge piece 34, onto which the operational element 12 is coupled, is provided on the same side as the grip surface 26 with respect to the mounting pin 32, there is provided in the illustrative example shown in FIG. 6 the bridge 34 on the opposite side of the mounting pin 32, which forms the pivot axis, relative to the grip surface 26. A depressing of the distal oriented actuation arm 36 of the second grip part 24 results, contrary to the illustrative examples in FIGS. 1–4, in a pulling action upon the operational element 12.

As further variants there is shown in the illustrative example shown in FIG. 6 a variant in which no locking mechanism is provided, which mechanism would prevent a return pivoting upon operation of the second grip part 24. In the illustrative example shown in FIG. 6 there is provided, however, a return spring 54 which is formed as a leaf spring, which on one end is fastened to the block of the receiving part 14, for example, by spot welding. With the other end the return spring 54 pushes against the inside surface of the grip surface 26 of the second grip part 24 in the area of the actuation arm 36. The return spring 54 thus operates upon both the actuation arm 36 to counter the exerted downward operating force as well as assists thereby the return movement of the jaws of the tubular shafted instrument to the starting position when the operator presses upon the return arm 38.

Figure 8:
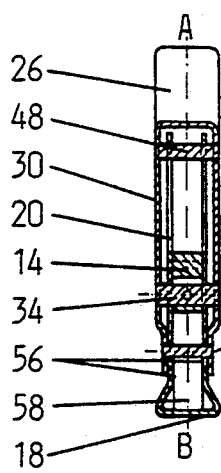
Figure 7:
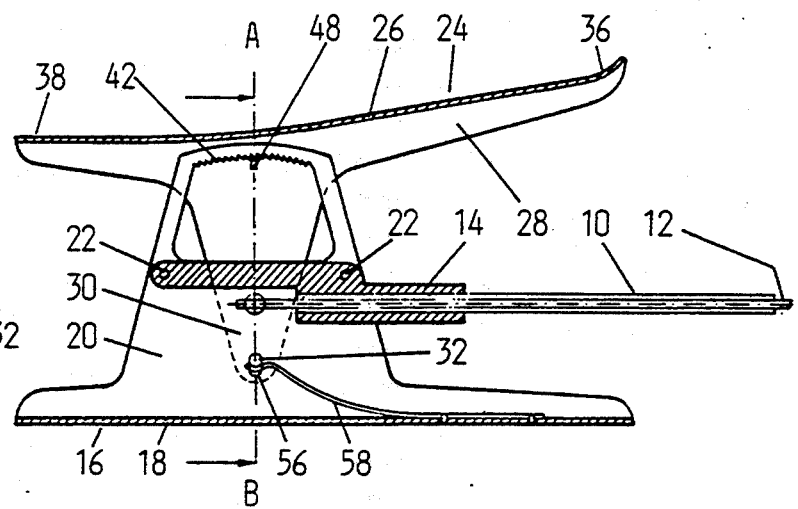

In the FIGS. 7 and 8 a fourth illustrative example of the grip is shown. Here also corresponding parts are indicated with the same reference numerals as previously, and reference is made to the relevant previous discussion.

In the illustrative examples of FIGS. 7 and 8 the shanks 20 of the first grip part 16 are drawn up to the inner side of the grip surface 26 of the second grip part 24. The shanks of the second grip part overlap with their attachment protrusion 30 the shanks 20 of the first grip part 16 from the outside. The mounting pin 32 is lodged in the attachment protrusion 30 and penetrates into the slotted hole 56 of the shank 20 of the first grip part 16. The slotted holes 56 are oriented horizontally to the grip surface 18 of the first grip part 16, so that the second grip part 24 by means of the in the slotted holes 56 lodged mounting pin 32 not only is pivotable as a rocker, but also that is has a stroke according to the measurement of the slotted holes 56 and can be correspondingly moved towards and away from the first grip part 16.

The shanks of the first grip part 16 display in their upper realm an internal cutout, which corresponds to the internal cutout of the frame member 40 in the illustrative examples shown in FIGS. 1-4 and 5. On the internal surface of the internal cutout which is oriented away from the grip surface 26 of the second grip part 24 the shanks 20 are provided with toothed locking ratchet 42. The detente latch 48 is in this embodiment firmly planted between the shanks 28 of the second grip part 24. A spring 58 in the form of a leaf spring is fastened with one end inside on the grip surface 18 of the first grip part 16, for example, by means of spot welding. With it's free end the spring 58 engages from underneath on the mounting pin 32, so that it urges the second grip part 24 away from the first grip part 16 and thereby holds the detente latch 48 in engagement with the locking ratchet 42.

By the depressing of the distal situated actuation arm 36 of the second grip part 24 the operational element 24 is pushed forwards in the shaft tube 10, in order to actuate the jaws of the tubular shafted instrument. The detente latch 48 thereby glides ratcheting over the teeth of locking ratchet 42. A return pivoting of the second grip part 24 is prevented by the detente latch 48 which is urged by means of the spring 58 into the teeth of locking ratchet 42. For releasing of the locking mechanism the operator presses the grip part 16 and 24 together against the force of the spring 58, so that the detente latch 48 is lifted out of the ratcheting teeth of locking ratchet 42. By means of pressure of the return arm 38 the second grip part 24 and thereby the jaws of the tubular shafted instrument can be brought back to the starting position.

Figure 9:
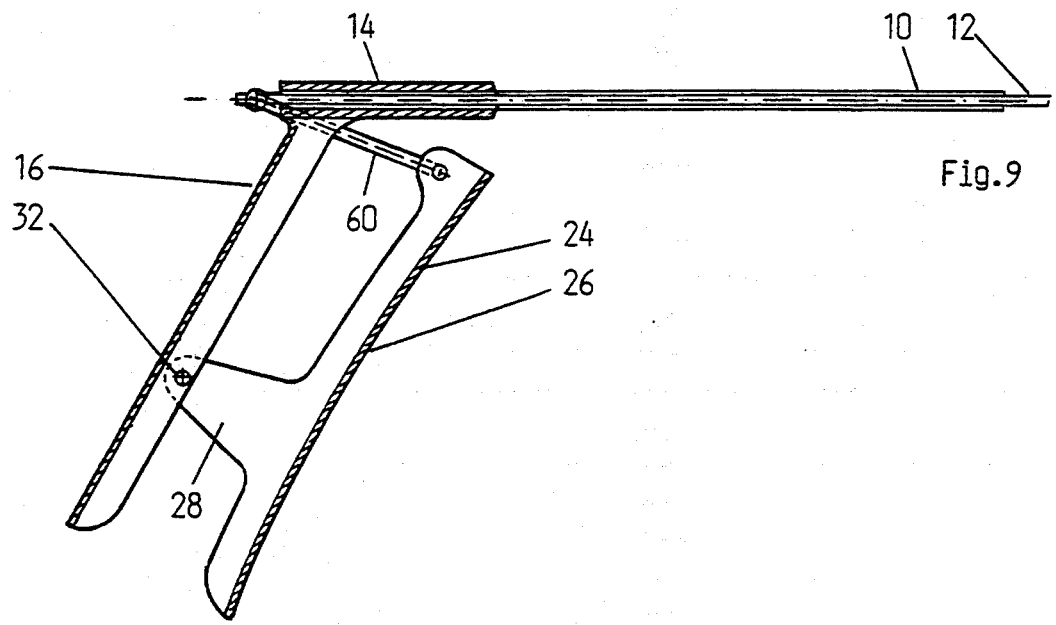

FIG. 9 lastly shows an illustrative example in which the grip parts 16 and 24 with their grip surfaces 18 and 26 are not situated parallel to the shaft tube 10, but rather are provided at an angle. On the free end of the actuator arm of the as rocker constructed second grip part 24 a hinge rod 60 is hinged, which on the other end is connected to the operational element 12. The illustrative example shown in FIG. 9 is designed for a pulling actuation of the jaws.

While the illustrative examples of FIGS. 1-4, FIG. 5 and FIGS. 7 and 8 having the locking mechanism are particularly suitable for the intended use in which the jaws of the shaft tool exercise a fixed, gripping or locking function, the illustrative examples of FIGS. 6 and 9 are particularly suited for applications such as those in which the jaws have a function of cutting or punching. It is of course also possible to provide in the form of the grip according to FIGS. 1-4, FIG. 5 or FIG. 7 and 8 a return spring according to FIG. 6, in order to assist in the returning to the rest position upon release of the locking mechanism.

Now that the invention has been described,
What is claimed is:

1. A grip for a surgical instrument, said surgical instrument comprising:
   a tubular shaft having a proximal end and a distal end,
   at least one articulated jaw mounted on said distal end of said tubular shaft,
   an elongated operational element slidably disposed in said tubular shaft and connected to said at least one articulated jaw,
   a hand grip comprising a first grip part having a grip surface for engagement with the palm of a hand and a second grip part having a grip surface for engagement with the fingers of the hand, said grip surfaces being spaced apart from each other,
   said first grip part fixedly connected to the proximal end of said tubular shaft,
   said second grip part constructed as a rocker comprising a pivot and first and second arms extending from said pivot, said rocker being connected at said pivot to said surgical instrument pivotably about a pivot axis which is perpendicular to the shaft tube, said first and second arms each having contact surfaces positioned for making contact with one or more fingers of the hand during gripping of said surgical instrument, said contact surfaces of said first and second arms each describing an angle of less than 30° with respect to said grip surface of said second grip part, said elongated operational element being connected to said rocker, such that pressing said first rocker arm towards said first grip part causes said second rocker arm to move away from said first grip part and causes said elongated operational element to move axially in a first, operational direction, and such that pressing said second rocker arm towards said first grip part causes said first rocker arm to move away from said first grip part and causes said elongated operational element to move axially in a second, return direction,
   wherein said shaft tube is set into a receiving part, said first grip part is securely mounted on said receiving part, and said second grip part is pivotally mounted, with respect to the first grip part, on the receiving part by means of a mounting pin,
   and wherein said receiving part is constructed as a block, wherein said grip parts are each provided with two shanks connected with the grip surfaces, and wherein said shanks embrace the receiving part.

2. A grip for a surgical instrument, said surgical instrument comprising
   a tubular shaft having a proximal end and a distal end,
   at least one articulated jaw mounted on said distal end of said tubular shaft,
   a first grip part which is fixedly connected to the proximal end of said tubular shaft,
   a second grip part mounted pivotally about a pivot axis which pivot axis is perpendicular to the shaft tube and
   an elongated operational element slidably disposed in said tubular shaft for conveying operational forces from said second grip part to at least one of said jaws, and
   a receiving part where in said shaft tube is set into said receiving part, said first grip part is securely mounted on said receiving part, and said second grip part is pivotally mounted, with respect to the first grip part, on the receiving part by means of a mounting pin,
   wherein said first grip part and said second grip part respectively exhibit grip contact surfaces which are spaced apart from each other and describe an angle of less than 30°,
   wherein said second grip part is constructed as a rocker with an actuation arm and a return arm and is pivotable about said pivot axis and is connected with the operational element in such a manner that upon pressure to the actuating arm or to the return arm the elongated operational element is axially displaced in said tubular shaft in an operational direction or a return direction, respectively, wherein said second grip part is further provided with a locking mechanism which resists movement in the return direction and which is manually releasable, said locking mechanism comprising a detente latch provided on the second grip part, a toothed locking ratchet provided in the first grip part, and a spring for biasing said detente latch to engage in engage in said toothed locking ratchet, said grip further comprising a frame member which engages said receiving part, said frame having an internal cutout, and wherein a toothed locking ratchet is provided on an internal edge of the cutout of the frame member which is facing away from the grip surface of the second grip part, wherein said grip parts are each provided with two shanks connected with the grip surfaces, wherein said shanks embrace the receiving part, and wherein said frame member engages the shanks of the first grip part between the shanks of the second grip part.

3. A grip for a surgical instrument as in claim 1, wherein said first grip part and said second grip part when at rest respectively exhibit grip contact surfaces which are essentially parallel to each other.

4. A grip for a surgical instrument as in claim 1, wherein said grip contact surface of said first grip part and said grip contact surface of said second grip part when at rest are provided essentially parallel to the shaft tube.

5. A grip for a surgical instrument as in claim 1, wherein said second grip part engages said elongated operational element by means of an attachment protrusion which extends essentially perpendicularly from said grip surface and extends along a plane through which said second grip pivots.

6. A grip for a surgical instrument as in claim 5, wherein said pivot axis is defined by a mounting pin which extends through the attachment protrusion of the second grip part, and wherein the elongated operational element is attached to the attachment protrusion at other than the axis of the mounting pin.

7. A grip for a surgical instrument as in claim 1, wherein said second grip part constructed as a rocker is constructed asymmetrically from the pivot axis, with a longer first arm forming an actuation arm and a shorter second arm forming a return arm.

8. A grip for a surgical instrument as in claim 1, wherein a spring means is provided for biasing said second grip part in one direction of pivotal movement.

9. A grip for a surgical instrument as in claim 1, wherein said second grip part is further provided with a locking means.

10. A grip for a surgical instrument as in claim 9, wherein said locking means is comprised of a detente latch provided on the second grip part, a toothed locking ratchet provided in the first grip part, and a spring for biasing said detente latch to engage in said toothed locking ratchet.

11. A grip for a surgical instrument as in claim 10, wherein said detente latch is connected to a latch lever which is pivotally mounted on the second grip part.

12. A grip for a surgical instrument as in claim 11, wherein said latch lever has a disengagement key for disengaging said latch lever, said disengagement key being provided at the grip surface of the second grip part.

13. A grip for a surgical instrument as in claim 12, wherein said disengagement key is provided in the grip surface in the area of the return arm, which return arm is provided directed opposingly to said actuation arm.

14. A grip for a surgical instrument as in claim 1, wherein a spring means is provided for biasing said second grip part in one direction of the pivotal movement, and wherein said spring is a leaf spring which braces itself at one end against said receiving part and at the other end on the inside of the second grip part.

15. A grip for a surgical instrument as in claim 1, wherein said second grip part is further provided with a locking means which resists movement in one direction and which is manually releasable, wherein said locking means is comprised of a detente latch provided on the second grip part, a toothed locking ratchet provided in the first grip part, and a spring for biasing said detente latch to engage in engage in said toothed locking ratchet, and wherein said toothed locking ratchet is provided on the receiving part or on the shank of the first receiving part.

16. A grip for a surgical instrument as in claim 2, wherein said detente latch is provided in operable association with a latch lever which is pivotally mounted on the second grip part, wherein said latch lever is pivotally mounted between the shanks of the second grip part.

17. A grip for a surgical instrument as in claim 16, wherein the second grip part is mounted movably towards the first grip part and is urged away from said first grip part by a spring pressure, wherein said detente latch is inserted securely between the shanks of the second grip part.

* * * * *